United States Patent
Kashikura et al.

(10) Patent No.: US 11,046,629 B2
(45) Date of Patent: Jun. 29, 2021

(54) METHOD OF PRODUCING COMPOUND HAVING BUTADIENE SKELETON CONTAINING HYDROGEN AND FLUORINE AND/OR CHLORINE

(71) Applicant: KANTO DENKA KOGYO CO., LTD., Tokyo (JP)

(72) Inventors: Wataru Kashikura, Shibukawa (JP); Yoshihiko Iketani, Shibukawa (JP); Ryo Kimura, Shibukawa (JP); Yukinobu Shibusawa, Shibukawa (JP)

(73) Assignee: KANTO DENKA KOGYO CO., LTD., Tokyo (JP)

( * ) Notice: Subject to any disclaimer, the term of this patent is extended or adjusted under 35 U.S.C. 154(b) by 0 days.

(21) Appl. No.: 16/959,317

(22) PCT Filed: Feb. 1, 2019

(86) PCT No.: PCT/JP2019/003558
§ 371 (c)(1),
(2) Date: Jun. 30, 2020

(87) PCT Pub. No.: WO2019/151467
PCT Pub. Date: Aug. 8, 2019

(65) Prior Publication Data
US 2021/0061735 A1  Mar. 4, 2021

(30) Foreign Application Priority Data
Feb. 2, 2018 (JP) .............................. JP2018-017570

(51) Int. Cl.
| | | |
|---|---|---|
| *C07C 17/266* | (2006.01) | |
| *C07C 17/269* | (2006.01) | |
| *C07C 17/275* | (2006.01) | |
| *C07C 17/278* | (2006.01) | |
| *C07C 17/281* | (2006.01) | |
| *C07C 17/263* | (2006.01) | |
| *C07B 61/00* | (2006.01) | |
| *C07C 21/20* | (2006.01) | |
| *C07C 17/26* | (2006.01) | |
| *C07C 17/272* | (2006.01) | |

(52) U.S. Cl.
CPC .......... *C07C 17/275* (2013.01); *C07C 17/263* (2013.01); *C07C 17/266* (2013.01); *C07C 17/269* (2013.01); *C07C 17/278* (2013.01); *C07C 17/281* (2013.01); *C07B 61/00* (2013.01); *C07C 17/26* (2013.01); *C07C 17/272* (2013.01); *C07C 21/20* (2013.01)

(58) Field of Classification Search
CPC ... C07C 17/278; C07C 17/275; C07C 17/269; C07C 17/281
See application file for complete search history.

(56) References Cited

U.S. PATENT DOCUMENTS

| | | |
|---|---|---|
| 3,983,179 A | 9/1976 | Riess et al. |
| 2008/0300432 A1 | 12/2008 | Hedrick et al. |

FOREIGN PATENT DOCUMENTS

| | | |
|---|---|---|
| JP | S50112307 A | 9/1975 |
| JP | 2008510832 A | 4/2008 |
| JP | 2016128415 A | 7/2016 |
| JP | 2017088665 A | 5/2017 |

OTHER PUBLICATIONS

Ehm, C. et al. "Fluorinated butadienes"Journal of Fluorine Chemistry 131 (2010) 1173-1181 (Year: 2010).*
Bach et al, "Crystal Structure Analysis of 1,1,4,4-Tetrafluorobutadiene and Experimental Determination of the Charge Density of 1,1,4,4-Tetrafluorobutatriene", Communications, pp. 296-299, Angew. ChenL Int. Ed. 2002, 41, No. 2.

(Continued)

*Primary Examiner* — Medhanit W Bahta
(74) *Attorney, Agent, or Firm* — Browdy and Neimark, PLLC

(57) ABSTRACT

An object of the present invention is to provide a simple, low-cost, and industrial method of producing a compound having a polyene skeleton containing hydrogen and fluorine and/or chlorine. A method of producing a halogenated diene represented by formula (1): $A^1A^2C=CA^3\text{-}CA^4=CA^5A^6$ [$A^1$, $A^2$, $A^5$, and $A^6$ are each independently hydrogen, fluorine, chlorine, a (perfluoro)alkyl group having 1 to 3 carbon atoms, or a (perfluoro)alkenyl group; $A^3$ and $A^4$ are each independently hydrogen, fluorine, or chlorine; at least one of $A^1$ to $A^6$ is hydrogen; at least one of $A^1$ to $A^6$ is fluorine or chlorine] comprises a step of subjecting the same or different halogenated olefin(s) represented by formula (2): $A^7A^8C=CA^9X$ [$A^7$ and $A^8$ are each independently hydrogen, fluorine, chlorine, a (perfluoro)alkyl group having 1 to 3 carbon atoms, or a (perfluoro)alkenyl group; $A^9$ is each independently hydrogen, fluorine, or chlorine; X is bromine or iodine] to a coupling reaction in the presence of a zero-valent metal and a metal salt.

7 Claims, No Drawings

(56) References Cited

OTHER PUBLICATIONS

Anderson et al., "Fluorodienes. I. Synthesis from Cyclobutenes", J. Am. Chem. Soc., 1961, 83, pp. 382-385.
Park, J.D. et al., "Preparation and some properties of certain fluorovinyl iodides and some fluorinated butadienes", Journal of Organic Chemistry, 1958, vol. 23, pp. 1661-1665, p. 1663, left col., line 30 to right col., line 8.
International Search Report of PCT/JP2019/003558, dated Jun. 18, 2019.

\* cited by examiner

METHOD OF PRODUCING COMPOUND HAVING BUTADIENE SKELETON CONTAINING HYDROGEN AND FLUORINE AND/OR CHLORINE

TECHNICAL FIELD

The present invention relates to a method of producing a compound having a polyene skeleton, especially butadiene skeleton, containing hydrogen and fluorine and/or chlorine.

BACKGROUND ART

As a synthetic method for a hydrofluorocarbon (HFC) compound having a 1,3-butadiene skeleton, a coupling reaction using two metals is known as in the following formula (Non Patent Literature (NPL) 1). In this reaction, 1,1-difluoroiodoethylene, as a starting material, is mixed with an excessive amount of metallic zinc, and then, the intended reaction is allowed to proceed through a coupling reaction using a catalytic amount of an expensive palladium catalyst.

[Formula 1]

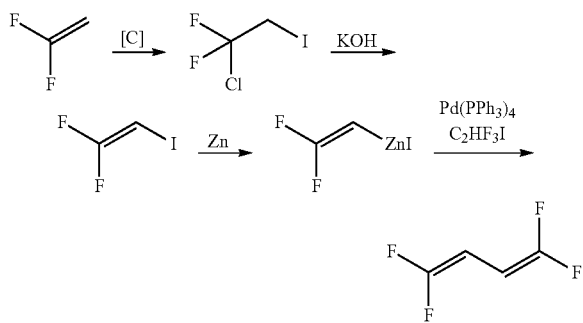

Moreover, it is known that 1,1,4,4-tetrafluoro-1,3-butadiene can be synthesized through a cyclization reaction between tetrafluoroethylene and acetylene, followed by pyrolysis as shown in the following formula. However, this cyclization reaction requires a high temperature of 600° C. (NPL 2).

[Formula 2]

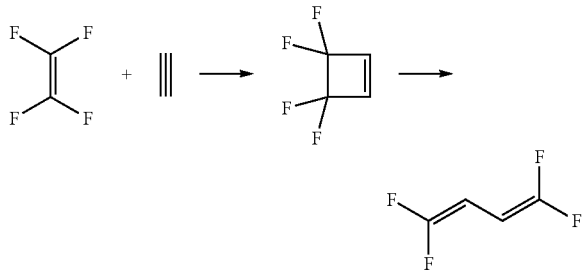

Further, as a production method for a fluorocarbon that bears no hydrogen atom bonded with a double bond, but not for a hydrofluorocarbon, hexafluoro-1,3-butadiene is obtained by reacting 1,1,2-trifluoro-2-iodoethylene with copper powder as shown in the following formula (Patent Literature (PTL) 1).

[Formula 3]

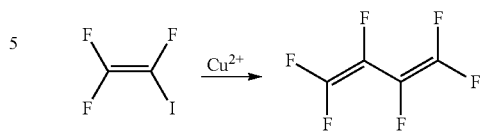

CITATION LIST

Patent Literature

PTL 1: Japanese Unexamined Patent Application Publication (Translation of PCT Application) No. 2008-510832

Non Patent Literature

NPL 1: Angew. Chem. Int. Ed., 2002, 41, 296-299
NPL 2: J. Am. Chem, Soc., 1961, 83, 382-385

SUMMARY OF INVENTION

Technical Problem

Neither of the above-described background art is considered to be usable for mass production of hydrofluorobutadiene due to the expensive metal catalyst, high-temperature reaction conditions, reaction substrate limited to perhalogenated ethylene, or the like. Meanwhile, the present inventors found a method of obtaining a hydrofluorobutadiene product (or 1,1,4,4-tetrafluorobutadiene) at a high yield of 88% by acting 4 equivalents of activated copper on 1,1-difluoroiodoethylene ($C_2HF_2I$) (Japanese Patent Application No. 2017-088665). However, the reaction requires 4 equivalents of a zero-valent metal relative to the reaction substrate. Accordingly, there was room for improvement in the amount of metal used.

An object of the present invention is to provide a simple, low-cost, and industrial method of producing a compound having a polyene skeleton, especially butadiene skeleton, containing hydrogen and fluorine and/or chlorine and, in particular, to provide a production method for hydrofluorobutadiene using a reduced amount of a zero-valent metal.

Solution to Problem

The present inventors conducted intensive studies to achieve the above-mentioned object and found, as a result, that hydrofluorobutadiene can be obtained at a high yield by using a reduced amount of a zero-valent metal in the presence of a metal salt in the reaction system, thereby completing the present invention. Specifically, the present invention provides the following.

[1] A method of producing a halogenated diene represented by formula (1):

[Formula 4]

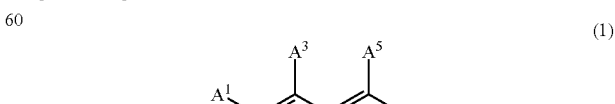

(1)

wherein: $A^1$, $A^2$, $A^5$ and $A^6$ are each independently hydrogen, fluorine, chlorine, a (perfluoro)alkyl group having 1 to 3 carbon atoms, or a (perfluoro)alkenyl group;

$A^3$ and $A^4$ are each independently hydrogen, fluorine, or chlorine; and at least one of $A^1$ to $A^6$ is hydrogen, and at least one of $A^1$ to $A^6$ is fluorine or chlorine.

the method comprising a step of subjecting the same or different halogenated olefin(s) represented by formula (2) to a coupling reaction in the presence of a zero-valent metal and a metal salt:

[Formula 5]

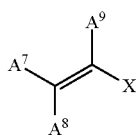

(2)

wherein: $A^7$ and $A^8$ are each independently hydrogen, fluorine, chlorine, a (perfluoro)alkyl group having 1 to 3 carbon atoms, or a (perfluoro)alkenyl group;

$A^9$ is each independently hydrogen, fluorine, or chlorine; and

X is bromine or iodine.

[2] The method according to [1], comprising the step of subjecting the same halogenated olefin to a coupling reaction.

[3] The method according to [1], comprising the step of subjecting the different halogenated olefins to a coupling reaction.

[4] The method according to any one of [1] to [3], where at least one of the halogenated olefin(s) represented by formula (2) is 1,1-difluoro-2-iodoethylene.

[5] The method according to any one of [1] to [4], where the zero-valent metal and a metal of the metal salt are copper.

[6] The method according to any one of [1] to [5], where the step of subjecting to a coupling reaction is performed in a solvent or in the absence of solvent.

[7] The method according to [6], where the solvent is one or more selected from amide solvents.

[8] The method according to any one of [1] to [7], where a reaction temperature in the step of subjecting to a coupling reaction is within a range of 20° C. to 200° C.

Advantageous Effects of Invention

The present invention enables high-yield, simple, low-cost, and industrial production of a halogenated diene represented by formula (1) having at least one hydrogen atom and at least one fluorine atom and/or chlorine atom. In particular, according to the present invention, it is possible to produce hydrofluorobutadiene using a reduced amount of a zero-valent metal.

DESCRIPTION OF EMBODIMENTS (Action)

The present invention is a method of producing a halogenated diene represented by formula (1) and is characterized by comprising a step of subjecting the same or different halogenated olefin(s) represented by formula (2) to a coupling reaction in the presence of a zero-valent metal and a metal salt.

As far as the applicants know, a reaction of coupling halogenated olefins whose double-bond carbons are bonded with one or more hydrogen atoms without using an expensive noble metal catalyst, rather by using a zero-valent metal and a metal salt, especially zero-valent copper and a copper salt, even in a small amount of metal (approximately 1 equivalent to the reaction substrate) had not been proposed. Under such circumstances, the present invention was experimentally found and is totally unpredictable to those skilled in the art.

(Reaction Substrates)

The reaction substrates of the present invention are halogenated olefins represented by formula (2). In formula (2), $A^7$ and $A^8$ are each independently hydrogen, fluorine, chlorine, a (perfluoro)alkyl group having 1 to 3 carbon atoms, or a (perfluoro)alkenyl group; $A^9$ is hydrogen, fluorine, or chlorine; and X is bromine or iodine. Two of the same or different such reaction substrate(s) are coupled at the sites bonded with X, thereby forming a halogenated diene represented by formula (1). Provided that at least one of $A^1$ to $A^6$ is hydrogen, and at least one of $A^1$ to $A^6$ is fluorine or chlorine in formula (1), two of the same or different halogenated olefin(s) represented by formula (2) are selected for reaction substrates. Here, examples of the (perfluoro)alkyl group having 1 to 3 carbon atoms include a trifluoromethyl group, a pentafluoroethyl group, an n-heptafluoropropyl group, and a heptafluoroisopropyl group. Although the carbon number is not limited, the (perfluoro)alkenyl group is desirably selected such that the number of double bonds in product polyenes becomes 2 to 6. Specific examples include a trifluorovinyl group, a 1,2,3,4,4-pentafluoro-1,3-butadienyl group, and a 1,2,3,4,5,6,6-heptafluoro-1,3,5-hexatrienyl group.

Specific examples of the halogenated olefin(s) represented by formula (2) include 1,1-difluoroiodoethylene, 1,2-difluoroiodoethylene, 2-fluoroiodoethylene, 1-fluoroiodoethylene, iodoethylene, 1,1-difluorobromoethylene, 1,1-dichloroiodoethylene, and 1,1,2-trifluoroiodoethylene.

(Zero-Valent Metals)

In the present invention, a zero-valent metal is required to be present in the reaction system as a catalyst. Examples of the metal include copper, zinc, magnesium, iron, silver, aluminum, and nickel, and copper is preferably used. To increase the surface area for reactions, the metal is preferably granular. In this case, the particle size is preferably 10 μm to 1 mm and more preferably about 20 to 80 μm, for example. Since the metal surface is generally oxidized, the catalyst activity is low. Accordingly, before feeding to the reaction system, the metal is preferably subjected to pre-treatment for removing ionized metal, such as oxides or nitrides, from the metal surface. An exemplary such pre-treatment includes mixing with an acid, stirring, filtering, washing with pure water and acetone, followed by heat vacuum drying, and the like.

(Metal Salts)

In the present invention, a metal salt, together with a zero-valent metal, is required to be present in the reaction system. Exemplary metals of the metal salt include the above-mentioned ones for the zero-valent metal. Examples of the metal salt include inorganic acid salts (acetates, trifluoromethanesulfonates (TfO—), carbonates, sulfates, and nitrates, for example) and halides (fluorides, bromides, chlorides, and iodides, for example) of copper, zinc, magnesium, iron, silver, aluminum, and nickel. Among these salts, copper halides are preferable, copper chloride is more preferable, and cuprous chloride (CuCl) and cupric chloride (CuCl$_2$) are particularly preferable. The zero-valent metal and a metal of the metal salt may be the same or different metal(s). Exemplary combinations of the zero-valent metal and the metal salt include a combination of zero-valent copper and a copper salt, in particular, a combination of zero-valent copper and cuprous chloride, and a combination of zero-valent copper and cupric chloride.

(Reaction Conditions)

The coupling reaction of the present invention is performed by heating a halogenated olefin or halogenated olefins represented by formula (2) in the presence of a zero-valent metal and a metal salt. The reaction temperature is preferably 20° C. to 200° C. and more preferably 100° C. to 150° C. The reaction pressure is typically atmospheric pressure, but when the reaction substrate is a gas, the reaction can be performed by placing the zero-valent metal and the metal salt inside a pressure-resistant reaction container and introducing the gas into the reaction container. The reaction can be terminated by lowering the reaction temperature to room temperature. The amount of the zero-valent metal is preferably 1 to 2 equivalents and more preferably 1 to 1.5 equivalents to the reaction substrate. Meanwhile, the metal salt is enough in an amount less than the zero-valent metal and the amount is preferably 0.1 to 10 mol % and more preferably 1 to 5 mol % relative to the amount (100 mol %) of the reaction substrate.

When the reaction substrate is a liquid, the coupling reaction is preferably performed in a solvent since the uniform reaction is possible. Exemplary solvents include amide solvents, and specifically, DMF (N,N-dimethylformamide), NMP (N-methyl-2-pyrrolidone), and so forth may be used.

The halogenated client of formula (1), which is the product of the present invention, may be purified by a method known in the relevant field and is commonly purified by distillation.

EXAMPLES (Copper Activation Method)

Copper powder was added to hydrochloric acid, mixed, suction filtered, and washed with pure water and then with acetone. The washed copper powder was subjected to heat vacuum drying at 150° C.

Example 1

To a round-bottom flask equipped with a mechanical stirrer, a thermometer, a condenser cooled to −20° C., and a trap, copper powder (particle size of about 20 to 40 μm, 120.25 g, 1.89 mol, 1.2 equivalents) activated by the above-described method, cupric chloride (0.060 mol or 3.8 mol % relative to the amount of 1,1-difluoroiodoethylene C$_2$HF$_2$I), and DMF (91 mL) were fed and heated to 130° C. in an oil bath. To the heated solution, 1,1-difluoroiodoethylene C$_2$HF$_2$I (301.14 g, 1.586 mol) synthesized in accordance with the method described in NPL 1 was added dropwise at a rate of 1 g/min. After the end of the dropwise addition, the temperature of the condenser was set to 5° C. and the reaction solution was stirred for 3 to 4 hours. Subsequently, the oil bath temperature was raised to 150° C., and the reaction solution was stirred for 30 minutes and then cooled to room temperature. The product had a boiling point of 4° C. to 5° C. and was a gas at normal temperature. The product was collected as a liquid by cooling the trap with dry ice/alcohol to about −70° C. Weighing and GC analysis of the collected gas (the amount of collected gas: 100 g, GC purity: 88%) revealed the yield of the product (1,1,4,4-tetrafluorobutadiene) of 88% as a crude percentage yield based on 1,1-difluoroiodoethylene.

Comparative Example 1

To a round-bottom flask equipped with a mechanical stirrer, a thermometer, a condenser cooled to −20° C., and a trap, copper powder (particle size of about 20 to 40 μm, 267.60 g, 4.21 mol, 4 equivalents) activated by the above-described method and DMF (198 mL) were fed and heated to 130° C. in an oil bath. To the heated solution, 1,1-difluoroiodoethylene C$_2$HF$_2$I (200.05 g, 1.05 mol) synthesized in accordance with the method described in NPL 1 was added dropwise at a rate of 1 g/min. After the end of the dropwise addition, the temperature of the condenser was set to 5° C. and the reaction solution was stirred for 3 to 4 hours. Subsequently, the oil bath temperature was raised to 150° C., and the reaction solution was stirred for 30 minutes and then cooled to room temperature. The product was collected in the same manner as Example 1. Weighing and GC analysis of the collected gas (the amount of collected gas: 67.5 g, GC purity: 88%) revealed the yield of the product (1,1,4,4-tetrafluorobutadiene) of 88% as a crude percentage yield based on 1,1-difluoroiodoethylene.

Comparative Example 2, Examples 2 to 4

Comparative Example 2 and Examples 2 to 4 were performed in the same manner as Example 1 except for changing the materials (C$_2$HF$_2$I, copper powder, copper salts) and their amounts used for the reaction as shown in the table below.

TABLE 1

| | | | | | | | | | | | | |
|---|---|---|---|---|---|---|---|---|---|---|---|---|
| | \multicolumn{12}{c}{Amount used} |
| | C$_2$HF$_2$I | | Cu | | | CuCl$_2$ | | Cu(OAc)2 | | Cu(OTf)2 | | DMF |
| | (g) | (mol) | (g) | (mol) | (eq.) | (g) | (mol) | (g) | (mol) | (g) | (mol) | (mL) |
| Comp. Ex. 2 | 30.01 | 0.158 | 12.06 | 0.19 | 1.2 | — | — | — | — | — | — | 15 |
| Ex. 2 | 301.14 | 1.586 | 120.25 | 1.89 | 1.2 | 10.66 | 0.0793 | — | — | — | — | 150 |

TABLE 1-continued

| | Amount used | | | | | | | | | | |
|---|---|---|---|---|---|---|---|---|---|---|---|
| | $C_2HF_2I$ | | Cu | | | $CuCl_2$ | | $Cu(OAc)_2$ | | $Cu(OTf)_2$ | DMF |
| | (g) | (mol) | (g) | (mol) | (eq.) | (g) | (mol) | (g) | (mol) | (g) | (mol) | (mL) |
| Ex. 3 | 30.4 | 0.16 | 12 | 0.19 | 1.2 | — | — | 1.43 | 0.0079 | — | — | 15 |
| Ex. 4 | 30.1 | 0.158 | 12.03 | 0.19 | 1.2 | — | — | — | — | 2.83 | 0.0078 | 15 |

Each product was recovered in the same manner as Example 1 and subjected to weighing (crude yield) and gas chromatograph (GC) analysis. The results are shown in the table below.

TABLE 2

| | GC area % | | | | | Crude yield | Crude percentage yield |
|---|---|---|---|---|---|---|---|
| | VdF | $CF_2$=CHCl | $C_4H_2F_4$ | $CF_2$=CHI | Others | (g) | (%) |
| Comp. Ex. 2 | 0.1 | 0.5 | 13.0 | 86.3 | 0.1 | 7.62 | 10 |
| Ex. 2 | 1.6 | 0.7 | 88.0 | 9.6 | 0.1 | 100 | 88 |
| Ex. 3 | 0.4 | 14.7 | 70.6 | 12.7 | 1.6 | 8.83 | 62 |
| Ex. 4 | 0.5 | 0.1 | 94.7 | 4.0 | 0.6 | 6.24 | 59 |

The crude percentage yield was determined by calculating [(crude yield×crude gas purity)/molecular weight of $C_4H_2F_4$]/(weight of starting material/molecular weight of $C_2HF_2I$) and multiplying the resulting value by 2. Here, the GC area % was used as the crude gas purity.

From Example 1 and Comparative Example 1, it is understood that a high product yield of 88% can be maintained by the presence of a small amount of a copper salt in the reaction system even when the amount of zero-valent copper used is reduced from 4 equivalents to 1.2 equivalents.

Examples 2 to 4 and Comparative Example 2 reveal that the yield also improved when copper acetate ($Cu(OAc)_2$) or copper trifluoromethanesulfonate ($Cu(OTf)_2$) was added compared with the case without such addition and was the highest when $CuCl_2$ was added. From these results, it is understood that a high product yield can be maintained by the presence of a small amount of various copper salts in the reaction system even when the amount of zero-valent copper used is reduced from 4 equivalents to 1.2 equivalents.

The invention claimed is:

1. A method of producing a halogenated diene represented by formula (1):

[Formula 1]

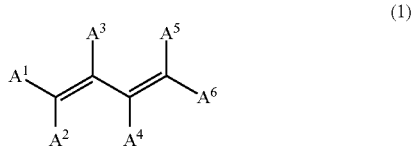

(1)

wherein: $A^1$, $A^2$, $A^5$, and $A^6$ are each independently hydrogen, fluorine, a (perfluoro)alkyl group having 1 to 3 carbon atoms, or a (perfluoro)alkenyl group;

$A^3$ and $A^4$ are each independently hydrogen or fluorine; and at least one of $A^1$ to $A^6$ is hydrogen, and at least one of $A^1$ to $A^6$ is fluorine, the method comprising a step of subjecting the same or different halogenated olefin(s) represented by formula (2) to a coupling reaction in the presence of a zero-valent metal and a metal salt:

[Formula 2]

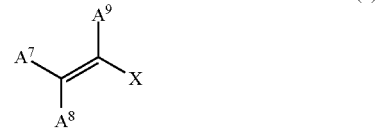

(2)

wherein: $A^7$ and $A^8$ are each independently hydrogen, fluorine, a (perfluoro)alkyl group having 1 to 3 carbon atoms, or a (perfluoro)alkenyl group;

$A^9$ is each independently hydrogen or fluorine; and

X is bromine or iodine, wherein the zero-valent metal and the metal of the metal salt are copper.

2. The method according to claim 1, comprising the step of subjecting the same halogenated olefin to a coupling reaction.

3. The method according to claim 1, comprising the step of subjecting the different halogenated olefins to a coupling reaction.

4. The method according to claim 1, wherein at least one of the halogenated olefin(s) represented by formula (2) is 1,1-difluoro-2-iodoethylene.

5. The method according to claim 1, wherein the step of subjecting to a coupling reaction is performed in a solvent or in the absence of solvent.

6. The method according to claim 5, wherein the solvent is present as one or more amide solvents.

7. The method according to claim 1, wherein a reaction temperature in the step of subjecting to a coupling reaction is within a range of 20° C. to 200° C.

* * * * *